US011723815B2

(12) United States Patent
Sablone

(10) Patent No.: US 11,723,815 B2
(45) Date of Patent: Aug. 15, 2023

(54) METHOD AND APPARATUS FOR PRODUCING ABSORBENT SANITARY ARTICLES, AND RELATIVE ABSORBENT SANITARY PRODUCT

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A., San Giovanni Teatino (IT)

(*) Notice: Subject to any disclaimer, the term of this patent is extended or adjusted under 35 U.S.C. 154(b) by 318 days.

(21) Appl. No.: 17/104,012

(22) Filed: Nov. 25, 2020

(65) Prior Publication Data

US 2021/0154053 A1 May 27, 2021

(30) Foreign Application Priority Data

Nov. 27, 2019 (IT) .................. 102019000022323

(51) Int. Cl.
 *B65H 35/04* (2006.01)
 *A61F 13/15* (2006.01)
 *A61F 13/49* (2006.01)
 *B65H 20/36* (2006.01)

(52) U.S. Cl.
 CPC .. *A61F 13/15756* (2013.01); *A61F 13/15723* (2013.01); *A61F 13/15764* (2013.01); *A61F 13/49011* (2013.01); *B65H 20/36* (2013.01); *B65H 35/04* (2013.01); *B65H 2801/57* (2013.01)

(58) Field of Classification Search
 CPC .... B65H 2801/57; B65H 35/04; B65H 20/36; A61F 13/49011; A61F 13/15764; A61F 13/15723; A61F 13/15756
 See application file for complete search history.

(56) References Cited

U.S. PATENT DOCUMENTS

2012/0061015 A1* 3/2012 Lavon ............... A61F 13/49015
 156/226
2015/0173957 A1* 6/2015 Schneider ......... A61F 13/15723
 493/374
2017/0304124 A1* 10/2017 Lenser .............. A61F 13/15747

FOREIGN PATENT DOCUMENTS

| CN | 107613922 A | 1/2018 | |
| EP | 3421022 A1 * | 1/2019 | ....... A61F 13/15585 |
| EP | 3421022 A1 | 1/2019 | |
| WO | 0047151 A1 | 8/2000 | |
| WO | WO-0047151 A1 * | 8/2000 | ....... A61F 13/49012 |

OTHER PUBLICATIONS

Italian Search Report dated Aug. 11, 2020. 8 pages.
Chinese Office Action dated Nov. 25, 2021. 10 pages.

* cited by examiner

*Primary Examiner* — Vishal I Patel
(74) *Attorney, Agent, or Firm* — RMCK Law Group PLC

(57) ABSTRACT

A method and apparatus for producing absorbent sanitary articles including an absorbent body having two front oblique sides and two rear oblique sides, and two longitudinal elastic bands attached to the absorbent body along said oblique sides, where each of said elastic bands includes a front section and a rear section separated from each other by transverse cuts and joined together by refastenable closure formations.

7 Claims, 9 Drawing Sheets

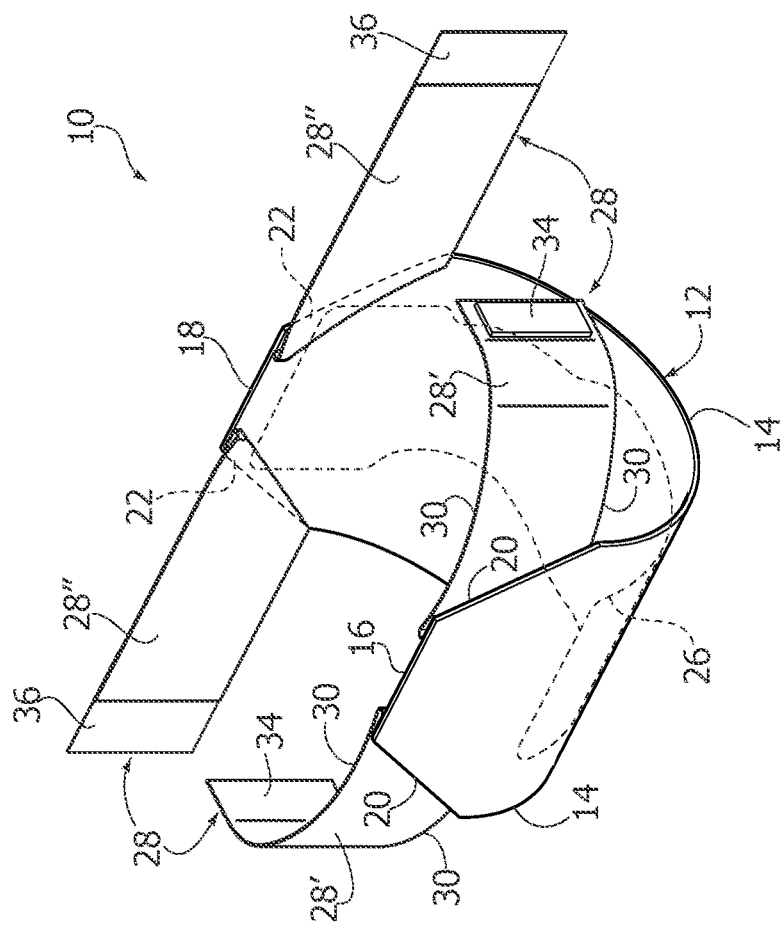
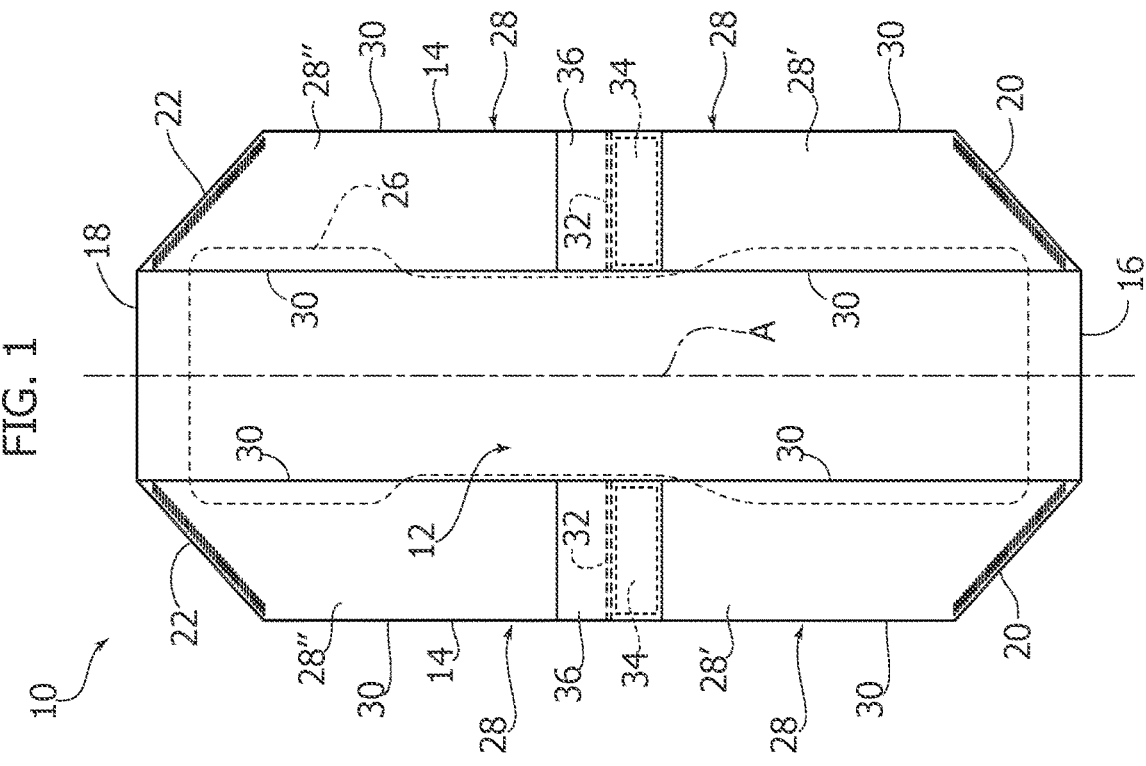

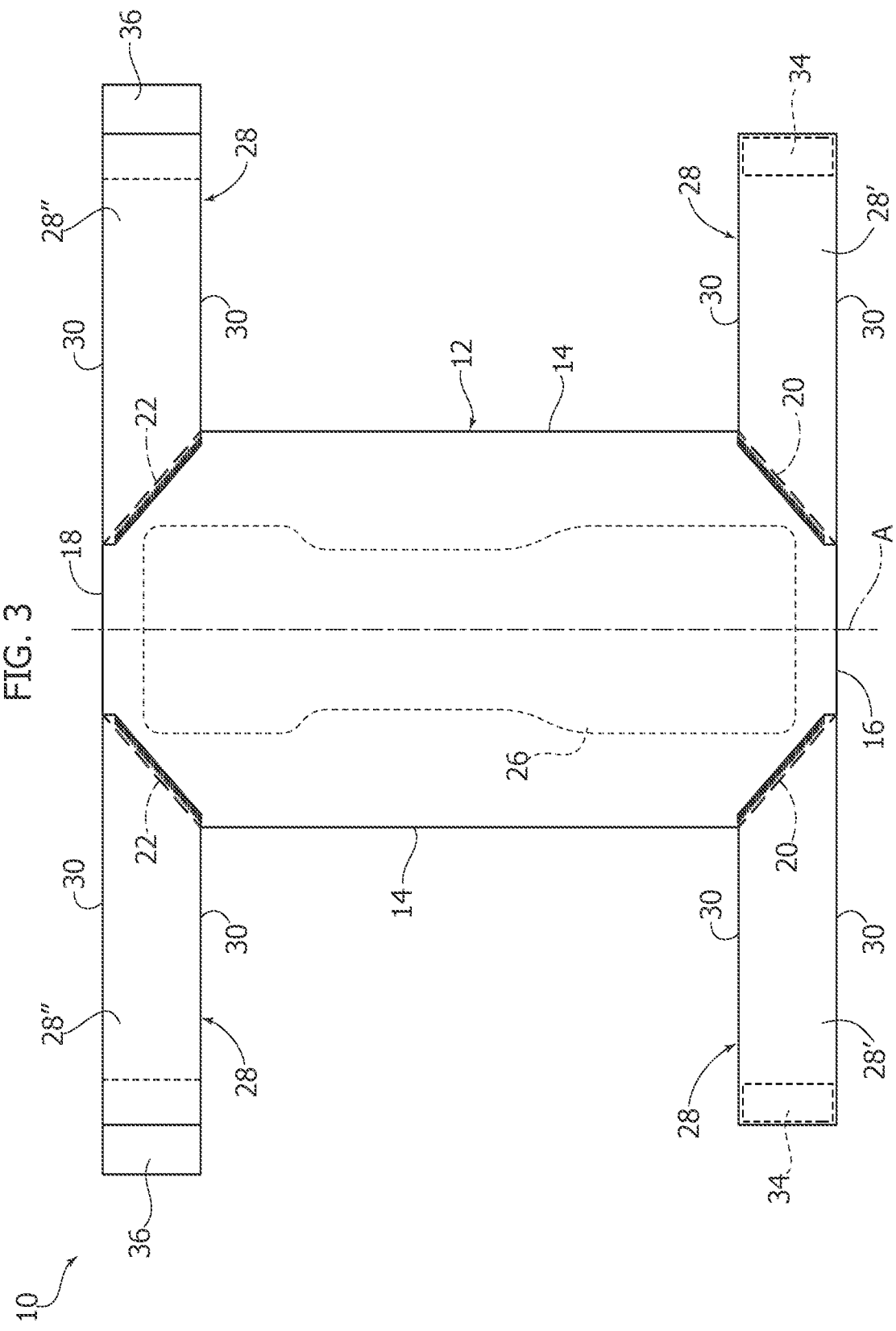

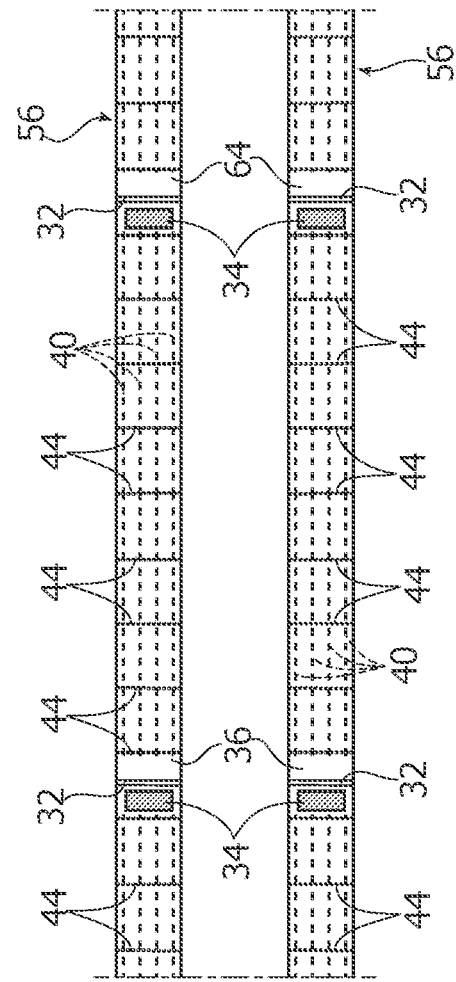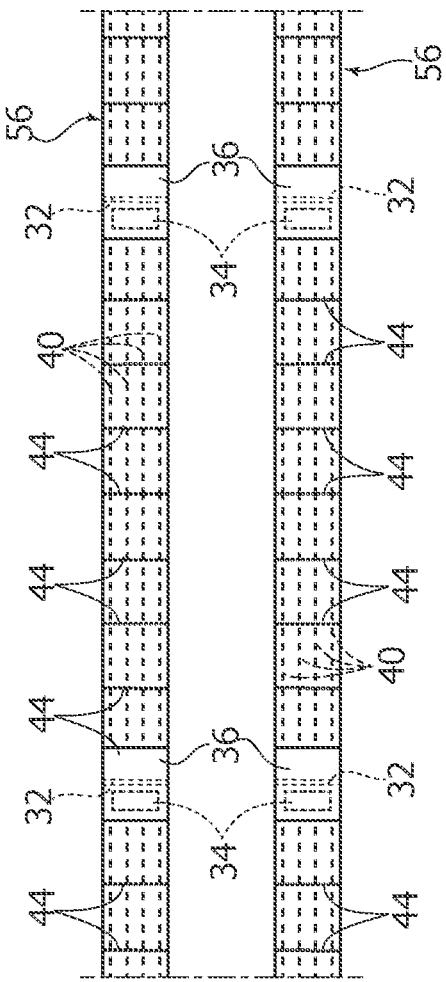

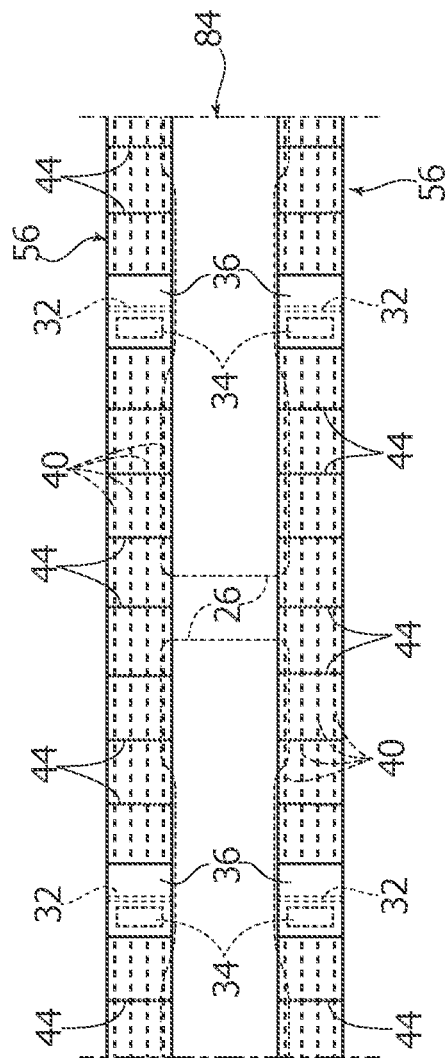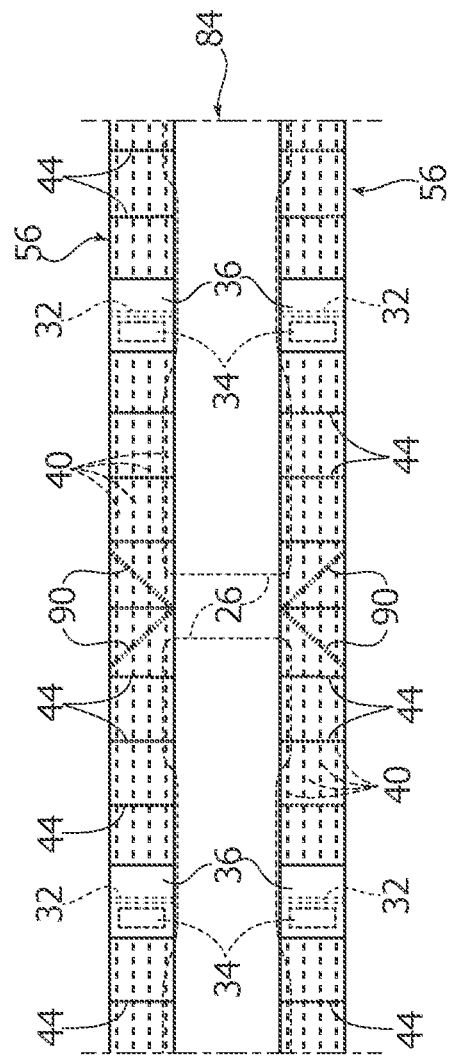

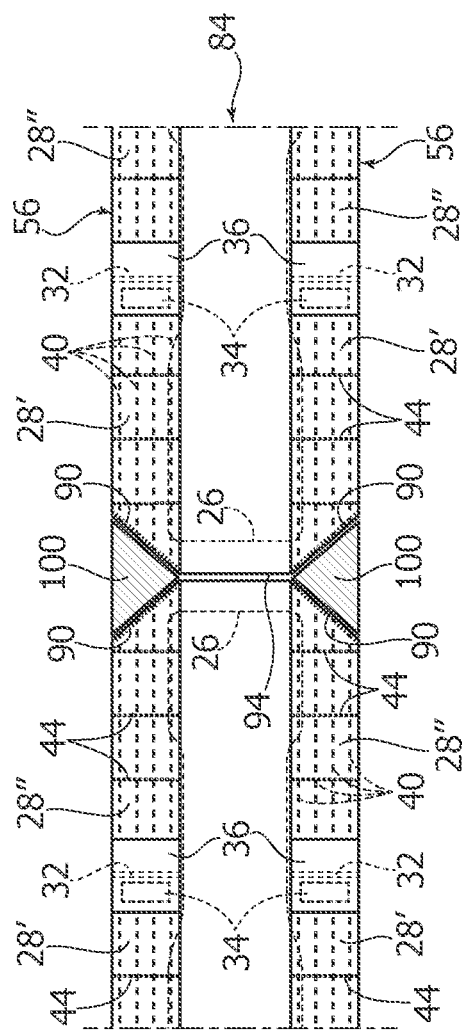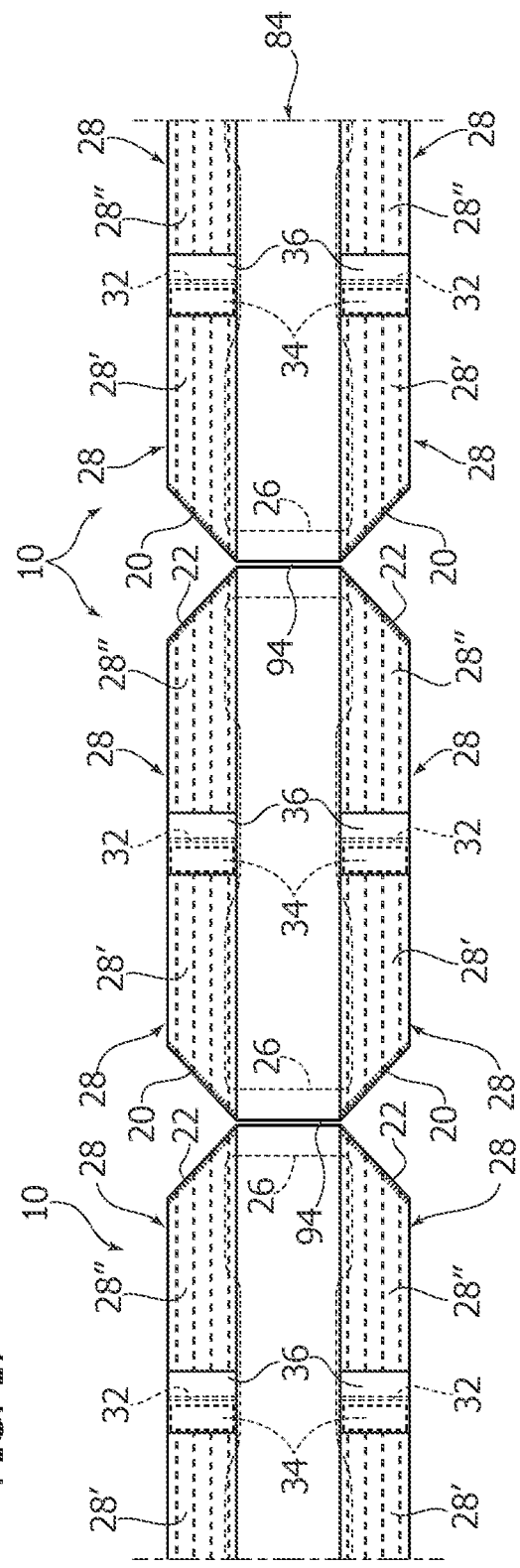

METHOD AND APPARATUS FOR PRODUCING ABSORBENT SANITARY ARTICLES, AND RELATIVE ABSORBENT SANITARY PRODUCT

CROSS-REFERENCE TO RELATED APPLICATION

This application claims priority to Italian Patent Application No. 102019000022323 filed Nov. 27, 2019. The disclosure of the above application is incorporated herein by reference in its entirety.

FIELD OF THE INVENTION

The present invention relates to a method and an apparatus for producing absorbent sanitary articles.

The invention was developed with particular regard to producing absorbent sanitary articles that can be worn as pants, such as the so-called training pants.

The invention specifically relates to producing absorbent sanitary articles of the openable and reclosable type.

The present invention relates, in particular, to a method and an apparatus for producing absorbent sanitary articles according to the so-called "Machine Direction" production technique.

DESCRIPTION OF THE PRIOR ART

The absorbent sanitary articles known as "training pants" are normally formed by an absorbent body having an elongated shape along a longitudinal axis, and two transverse waistbands (a front waistband and a rear waistband) applied to opposite ends of the absorbent body on the surface that faces, during use, towards the clothing. The transverse waistbands may be elasticized and can be fixed to each other permanently or by refastenable closure formations.

For producing absorbent sanitary articles composed of an absorbent body of elongated shape and two transverse waistbands, a production technique called "Cross Direction" is normally used, which consists of forming two continuous elastic parallel sheets, forming the front and rear waistbands, which advance in a machine direction and applying the absorbent bodies transversally between the continuous sheets. The absorbent bodies oriented transversely with respect to the machine direction are fixed at their opposite ends to the continuous sheets forming the waistbands.

Document WO2000/047151 A1 describes a method for producing absorbent sanitary articles of the type named "training pants" according to the Machine Direction production technique. The method described in this document envisages the formation of a continuous absorbent composite sheet that advances in a machine direction, in the direction of its longitudinal axis. Two continuous elastic bands are overlapped on respective longitudinal side edges of the continuous absorbent composite sheet. The continuous elastic bands are fixed to the continuous absorbent composite sheet along oblique junction lines with a V-shape open outwards. The method involves cutting the continuous composite sheet and the elastic bands along cutting lines in the shape of a double Y, so as to give rise to discrete absorbent sanitary articles each consisting of an absorbent body and two longitudinal elastic bands fixed at opposite ends of the absorbent body along oblique sides.

The solution known from WO2000/047151 provides absorbent sanitary articles which are permanently closed and shaped like pants. The method described in WO2000/047151 cannot be used in the case in which refastenable absorbent sanitary articles are required, which are increasingly requested on the market by virtue of their greater convenience of use.

OBJECT AND SUMMARY OF THE INVENTION

The present invention aims to provide a method and an apparatus for producing absorbent sanitary articles that overcome the problems of the prior art.

In particular, the present invention aims to provide a method and an apparatus for producing refastenable absorbent sanitary articles composed of an absorbent body with an elongated shape and two elastic waistbands parallel to the longitudinal axis of the absorbent body.

According to the present invention, this object is achieved by a method and by an apparatus having the characteristics forming the subject of claims 1 and 6.

According to another aspect, the present invention relates to an absorbent sanitary article having the characteristics forming the subject of claim 8.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein:

FIG. 1 is a plan view of an absorbent sanitary article according to the present invention in an extended configuration, FIG. 2 is a perspective view of the absorbent sanitary article of FIG. 1 in a configuration of use, FIG. 3 is a plan view of the absorbent sanitary article of FIGS. 1 and 2 in an extended position and with the elastic bands open, FIGS. 5-10 are schematic plan views illustrating various steps of a method for producing elastic bands, corresponding to the positions indicated by the arrows V-X of FIG. 4, FIGS. 12-17 are schematic plan views illustrating various steps of a method for producing absorbent sanitary articles, corresponding to the positions of the apparatus indicated by arrows XII-XVII of FIG. 11.

Figure 4:
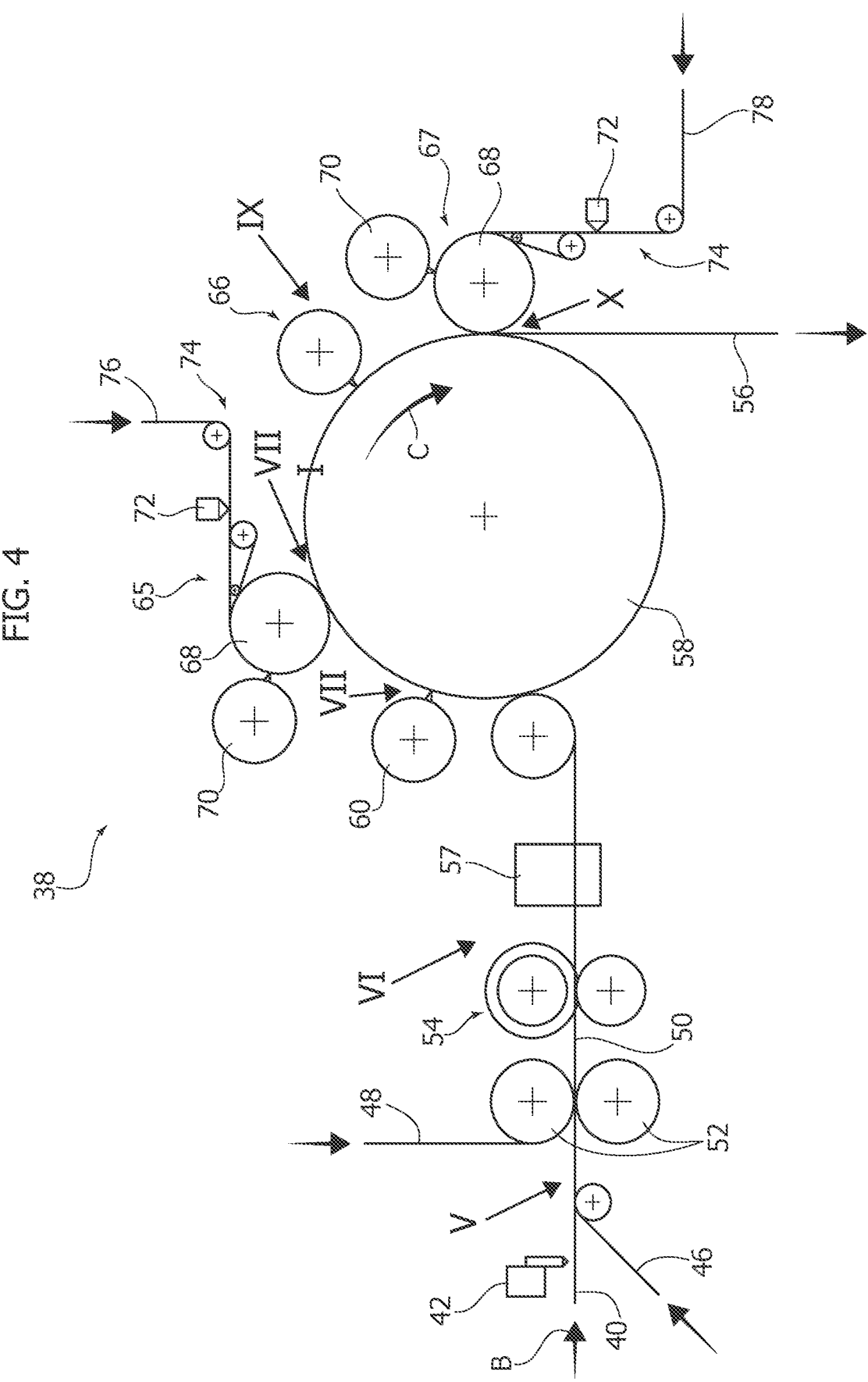
FIG. 4 is a schematic side view of a unit for producing elastic bands.

It will be appreciated that the various figures may not be represented on the same scale. It will also be appreciated that some elements or components have not been shown to simplify the understanding of the figures.

DETAILED DESCRIPTION

With reference to FIGS. 1-3, numeral 10 indicates an absorbent sanitary article according to an embodiment of the present invention. The absorbent sanitary article 10 illustrated by way of example in FIG. 1 represents refastenable training pants. However, it is understood that the present invention may also apply to absorbent sanitary articles of another type, for example, incontinence pads for adults.

The absorbent sanitary article 10 comprises an absorbent body 12 having an elongated shape along a longitudinal axis A. The absorbent body 12 has two longitudinal sides 14 that extend along a direction generally parallel to the longitudinal axis A. The longitudinal sides 14 may be straight, as illustrated by way of example in the figures, or they may be shaped in different ways. The absorbent body 12 comprises a front transverse side 16 and a rear transverse side 18. The absorbent body 12 also comprises two front oblique sides 20 and two rear oblique sides 22. The two front oblique sides 20 and the two rear oblique sides 22 may be symmetrical with respect to the longitudinal axis A. Each of the oblique sides 20, 22 connects one end of the respective front transverse side 16 or the respective rear transverse side 18 to a corresponding end of the respective longitudinal side 14.

The absorbent body 12 may comprise an absorbent core 26, which may be sandwiched between an inner sheet of liquid-permeable material (topsheet) and an outer sheet of impermeable material (backsheet). Additional absorbent layers may be comprised between the inner sheet and the outer sheet of the absorbent body 12 such as, for example, an Acquisition Diffusion Layer of the liquids, commonly referred to as ADL. The inner sheet or topsheet of the absorbent body 12 has a surface intended to face, during use, towards the user's body. The absorbent body 12 may comprise additional components (not illustrated) as is customary in the field, such as, for example, elastic elements for the legs (leg cuffs) applied onto the inner sheet and extending parallelly to the longitudinal axis A.

The absorbent sanitary article 10 comprises two elastic waistbands 28 located on opposite sides of the longitudinal axis A. Each of the two elastic waistbands 28 has two longitudinal sides 30 which, in the extended position of FIG. 1, extend in the direction of the longitudinal axis A. Each of the two elastic waistbands 28 has a front oblique side overlapping and fixed to the corresponding front oblique side 20 of the absorbent body 12, and an overlapping rear oblique side fixed to a corresponding rear oblique side 22 of the absorbent body 12. In the extended configuration of FIG. 1, each elastic waistband 28 extends in the direction of the longitudinal axis A between a front oblique side 20 and a corresponding rear oblique side 22 and overlaps on a corresponding side strip of the absorbent body 12. In a possible embodiment, the outer longitudinal sides 30 of the elastic waistbands 28 may be aligned with the longitudinal sides 14 of the absorbent body 12.

At least one of the two elastic waistbands 28 includes a front section 28' and a rear section 28" separated from each other by a transverse cut indicated by 32 in FIG. 1.

The front section 28' and the rear section 28" of at least one of the two elastic bands 28 are joined together by refastenable closure formations 34, 36. The refastenable closure formations 34, 36 are fixed to respective sections 28', 28" of the respective elastic band 28. A first closure formation 34 extends on the surface of a single section 28' and the second closure formation 36 extends over the transverse cut 32. The closure formations 34, 36 may comprise adhesive, or "hook-and-loop" mechanical attachment means, or their combinations. In a possible embodiment, the closure formation 34 applied on the front section 28' may be a closure formation of the loop type and the closure formation 36 fixed to the rear section 28" may be a closure formation of the hook type. The closure formations 34, 36 of each elastic band 28, when coupled together, establish the continuity of each elastic band 28 through the transverse cut 32.

In a possible embodiment, each of the elastic waistbands 28 comprises a respective front section 28' and a respective rear section 28" separated from each other by a transverse cut 32 and joined together by refastenable closure formations 34, 36.

When the closure formations 34, 36 are coupled together, the absorbent sanitary article 10 has a closed pant-like conformation, and the elastic waistbands 28 form part of the waistband of the garment. The closure formations 34, 36 may be separated from each other to allow opening of the absorbent sanitary article 10 along the elastic waistbands 28, as illustrated in FIGS. 2 and 3.

According to a possible embodiment, the closure formations 34, 36 are fixed on non-elastic end portions of the respective sections 28', 28". The closure formations 32, 34 may be fixed to the respective sections 28', 28" of the elastic bands 28 by glue or, alternatively, by welding. With reference to FIGS. 4-17, a possible embodiment of a method and an apparatus for producing an absorbent sanitary article 10 of the type illustrated in FIGS. 1-3 will now be described.

Figure 11:
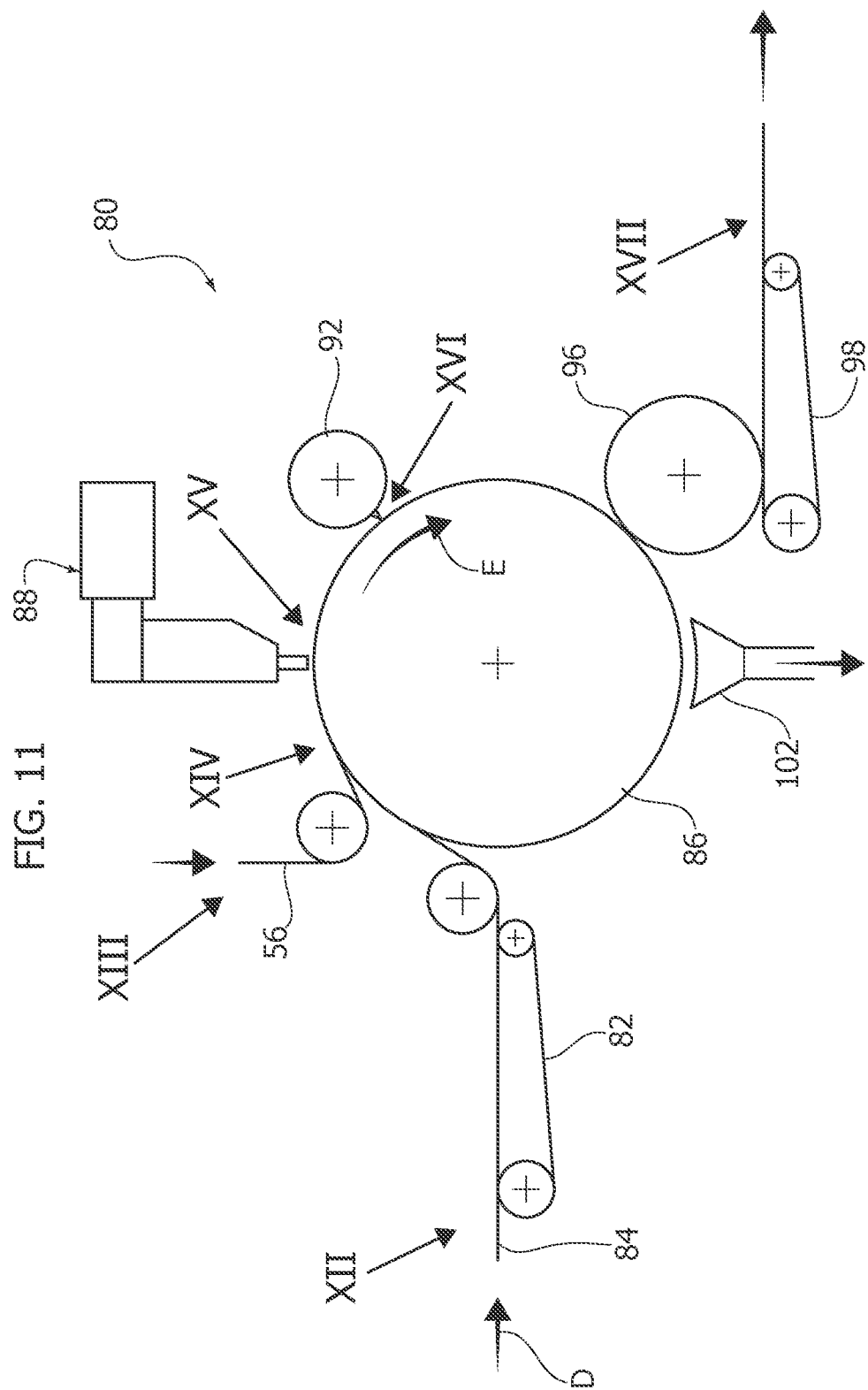
FIG. 11 is a schematic side view of a unit for applying elastic bands onto a continuous composite web.

The method involves forming two elastic bands having an indefinite extension in the longitudinal direction in the unit illustrated in FIG. 4, and applying the elastic bands onto a continuous absorbent composite web in the unit illustrated in FIG. 11.

The operations and units for forming the elastic bands and the operations and units for applying the elastic bands onto a continuous absorbent composite web will be described separately below.

Figure 5:
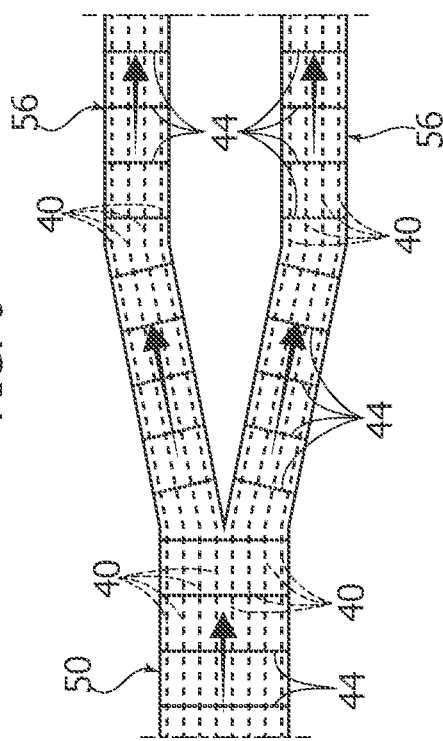

With reference to FIG. 4, numeral 38 indicates—in its entirety—an elastic band forming unit. A plurality of parallel elastic threads 40 are fed—in a tensioned state—in a longitudinal direction, in the direction indicated by the arrow B. A glue applicator 42 intermittently applies transverse strips of glue onto the elastic threads 40, said strips indicated by 44 in FIG. 5, spaced apart in the longitudinal direction of the elastic threads 40. The elastic threads 40 are enclosed between two non-elastic sheets 46, 48, for example, of non-woven fabric, so as to form a continuous elastic band 50 (FIG. 5). A pair of pressure rollers 52 presses the non-elastic sheets 46, 48 and the elastic threads 40 together. The elastic threads 40 are fixed to the non-elastic sheets 46, 48 along the transverse strips 44 on which the glue has been applied.

Figure 6:
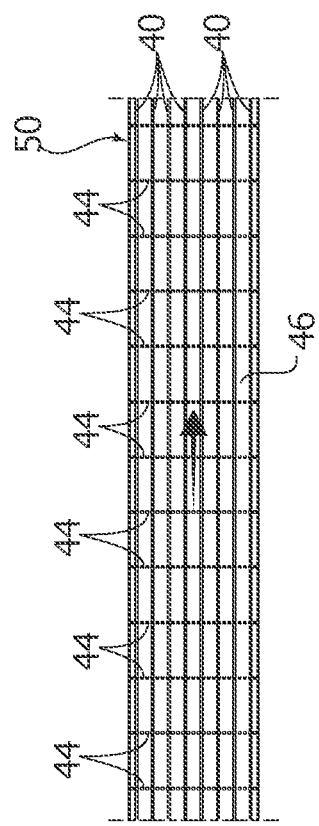

With reference to FIGS. 4 and 6, the continuous elastic band 50—downstream of the pressure rollers 52—is cut in the longitudinal direction, by a longitudinal cutting unit 54, so as to give rise to two elastic bands 56. A spacer unit 57 envisages the spacing apart of the two elastic bands 56 in a transverse direction, and arranging the two elastic bands 56 parallel to each other and at a predetermined distance. The elastic bands 56 spaced from each other in the transverse direction are fed onto the outer surface of a wheel 58 rotatable in the direction indicated by the arrow C.

Figure 7:
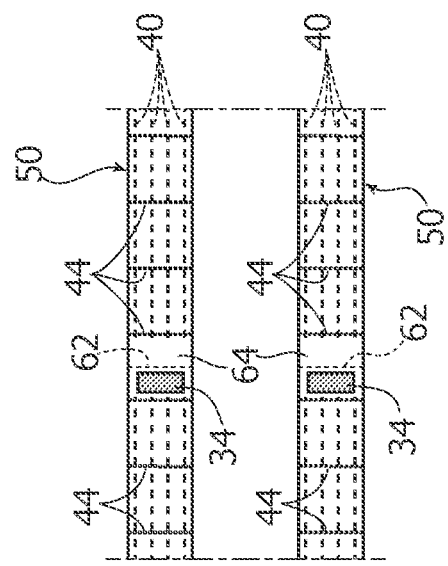

With reference to FIGS. 4 and 7, a first cutting device 60 cooperates with the outer surface of the wheel 58, and carries out the transverse cutting of the elastic threads 40 of the two elastic bands 56 at regular intervals. The transverse cutting of the elastic threads 40 is schematically indicated by 62 in FIG. 7, and is located in an intermediate position between two adjacent strips of glue 44. In a possible embodiment, the cutting device 60 may be configured to transversely cut only the elastic threads 40, without cutting the non-elastic sheets 46, 48. With reference to FIG. 7, following the transverse cutting of the elastic threads 40 along the transverse lines 62, the elastic threads 40 retract in the longitudinal direction up to the transverse fastening lines 44 adjacent to the cutting lines 62, thus forming non-elastic areas 64 on each of the elastic bands 56. The non-elastic areas 64 of each elastic band 56 are spaced apart at regular intervals in the longitudinal direction. Each of the non-elastic areas 64 is comprised between two transverse fastening lines 44 adjacent to the cutting line 62 of the elastic bands.

With reference to FIG. 4, the elastic band forming unit 38 comprises a first closure formation applying unit 65 and a second closure formation applying unit 67, which both cooperate with the wheel 58. The first closure formation applying unit 65 is located immediately downstream of the cutting device 60 of the elastic bands. A second cutting device 66 configured to carry out the transverse cutting of the elastic bands 56, at regular intervals, is arranged between the first closure formation applying unit 65 and the second closure formations applying unit 67.

Each of the two closure formation applying units 65, comprises an applicator roller 68 cooperating with a cutting roller 70, a glue applicator 72, and a web material feeder 74 configured to feed two continuous webs 76, 78 to the applicator roller 68, from which successive pairs of first closure formations 34 and second closure formations 36 are cut.

Figure 8:
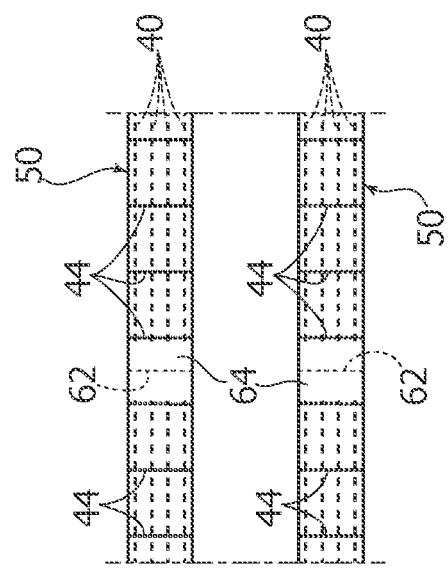

With reference to FIGS. 4 and 8, the first closure formation applying unit 65 applies first closure formations 34 onto the elastic bands 56, which may be fixed onto the elastic bands 56 by the glue applied by the glue applicator 72. The first closure formations 34 may be applied onto the non-elastic areas 64, and may occupy only a part of the respective non-elastic areas 64.

With reference to FIGS. 4 and 9, the transverse cutting unit 66 makes transverse cuts 32 on the elastic bands 56, which extend through the non-elastic areas 64 and are adjacent to the first closure formations 34. Following the transverse cuts 32, the elastic bands 56 are divided into a succession of elastic sections separated from each other.

With reference to FIGS. 4 and 10, after executing the transverse cuts 32, the second closure formation applying unit 67 applies the second closure formations 36 onto the elastic bands 56. The second closure formations 36 may be applied on respective non-elastic areas 64. The second closure formations 36 may be attached by a layer of glue applied by the glue applicator 72. Each of the second closure formations 36 extends over a respective transverse cut 32, and is engaged in the corresponding first closure formation 34. The second closure formations 36 re-establish the continuity of the elastic sections separated from each other by the transverse cuts 32.

Downstream of the second closure formation applying unit 67 the two elastic bands 56 having the shape illustrated in FIG. 10 are detached from the surface of the wheel 58 and are fed to an elastic band applying unit, indicated—in its entirety—by 80 in FIG. 11.

Figure 12:
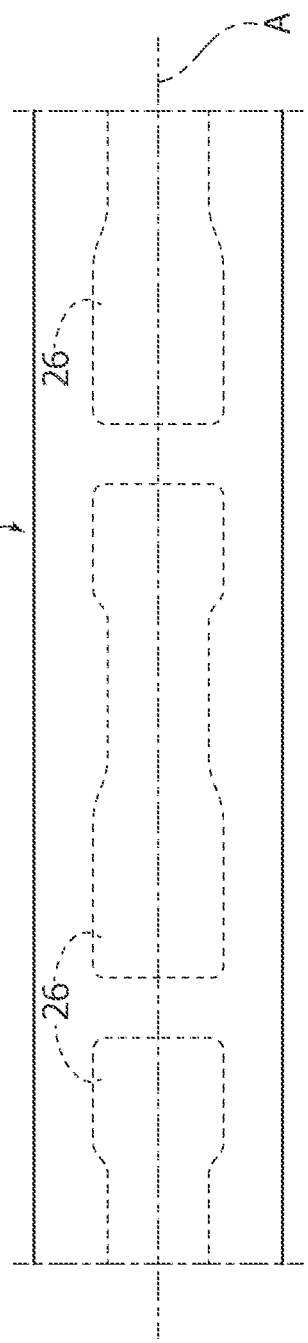

With reference to FIGS. 11 and 12, the elastic band applying unit 80 comprises a conveyor 82 that advances a continuous absorbent composite web 84 in the direction D. With reference to FIG. 12, the continuous absorbent composite web 84 may comprise a plurality of absorbent cores 26 oriented parallelly to the longitudinal direction A of the continuous absorbent composite web 84 and sandwiched between a topsheet and a backsheet. The conveyor 82 feeds the continuous absorbent composite web 84 onto the surface of a wheel 86 that is rotatable in the direction indicated by the arrow E.

Figure 13:
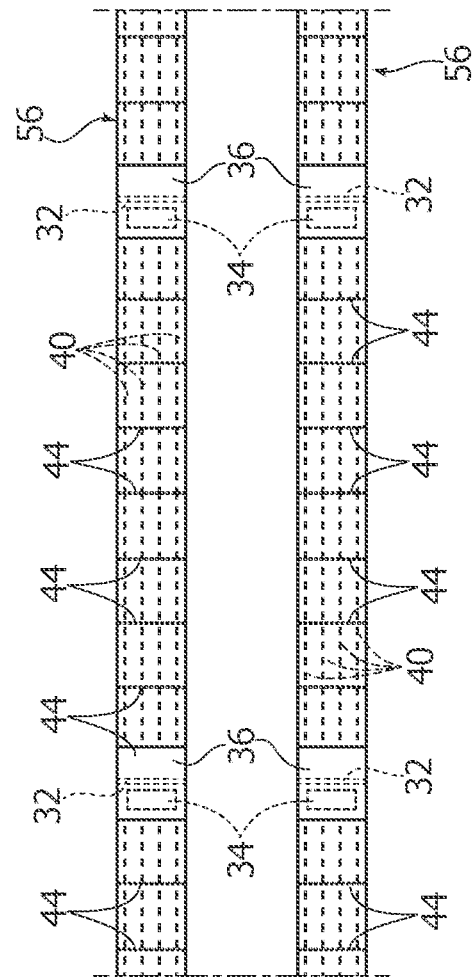

With reference to FIGS. 11 and 13, the two elastic bands 56 coming from the elastic band forming unit 38 are fed onto the surface of the wheel 86. With reference to FIGS. 11 and 14, the elastic bands 56 are applied onto the continuous absorbent composite web 84 as it advances on the surface of the wheel 86, and are overlapped on respective side portions of the continuous composite web 84. The elastic bands 56 are arranged in a predetermined phase relationship with respect to the continuous absorbent composite web 84.

With reference to FIGS. 11 and 15, the elastic band applying unit 80 comprises a welding unit 88, which is configured to attach the elastic bands 56 to the continuous absorbent composite web 84 along junction lines 90. The junction lines 90 are inclined with respect to the longitudinal axis A. The junction lines 90 may be straight or entirely or partly curved. In a possible embodiment, the junction lines may have a V shape open outwards. With reference to FIG. 15, the junction lines 90 may be located in an intermediate position between successive pairs of closure formations 34, 36. The junction lines 90 may be symmetrical with respect to a transverse line which is arranged between two successive absorbent cores 26 of the continuous absorbent composite web 84.

With reference to FIGS. 11 and 16, the elastic band applying unit 80 comprises a cutting device 92 cooperating with the wheel 86, and configured to cut the continuous absorbent composite web 84 and the elastic bands 56 along cutting lines at regular intervals 94. In a possible embodiment, the cutting lines 94 may have a double Y shape. The cutting lines 94 may have V-shaped oblique sections that may be flush with the junction lines 90 and transverse sections that join together the vertices of the V-shaped sections. The cutting lines divide the continuous absorbent composite web 84 and the elastic bands 56 into a succession of absorbent sanitary articles 10 (FIG. 17), each having the structure previously described with reference to FIG. 1. The absorbent sanitary articles 10 are detached from the surface of the wheel 86 by a release roller 96, and are deposited on an outlet conveyor 98. The double Y-shaped cutting lines 94 form triangular-shaped scraps 100 (FIG. 16), which are retained by suction on the surface of the wheel 86 and are removed and discarded into a scrap collection channel indicated schematically by 102 in FIG. 11. The double Y-shaped cutting lines 94 divide the continuous elastic bands 56 into a succession of discrete elastic waistbands 28, each of which is formed by two elastic sections 28', 28" separated from each other by the transverse cuts 32, and joined together by the refastenable closure formations 34, 36.

Of course, without prejudice to the principle of the invention, the details of construction and the embodiments can be widely varied with respect to those described and illustrated, without thereby departing from the scope of the invention as defined by the claims that follow.

The invention claimed is:

1. A method for producing absorbent sanitary articles, comprising:
    providing a continuous absorbent composite web having a longitudinal axis,
    advancing said continuous absorbent composite web in a direction of said longitudinal axis,
    forming two elastic bands having an indefinite extension in a longitudinal direction, at least one of which comprises a succession of elastic sections separated from each other by transverse cuts and joined together by refastenable closure formations,
    overlapping said elastic bands on respective side portions of the continuous absorbent composite web,
    fixing the elastic bands to the continuous absorbent composite web along junction lines inclined with respect to the longitudinal axis, and
    cutting the continuous absorbent composite web and the elastic bands along cutting lines, so as to give rise to a succession of absorbent sanitary articles each having an absorbent body elongated in the longitudinal direction, having two front oblique sides and two rear oblique sides, and two elastic waistbands fixed to the absorbent body along said front and rear oblique sides, wherein at least one elastic waistband has a front section and a rear section separated from each other by a transverse cut and joined together by refastenable closure formations.

2. The method according to claim 1, comprising:

forming non-elastic areas on at least one of said elastic bands, fixing first closure formations of the closure formations to said non-elastic areas, transversely cutting said elastic bands through said non-elastic areas, and fixing second closure formations of the closure formations to said non-elastic areas, said second closure formations extending at said transverse cuts and engaging said first closure formations in a refastenable manner.

3. The method according to claim 1, wherein each of said elastic waistbands has a respective front section and a respective rear section separated from each other by a transverse cut and joined together by the refastenable closure formations.

4. The method according to claim 1, wherein said junction lines inclined with respect to the longitudinal axis have a V-shape opening outwards.

5. The method according to claim 2, wherein the step of forming non-elastic areas on said elastic bands is carried out by a transverse cut of longitudinal elastic threads of said elastic bands.

6. An apparatus for producing absorbent sanitary articles, comprising:

a conveyor configured to advance a continuous absorbent composite web in a longitudinal direction, the continuous absorbent composite web having a longitudinal axis, an elastic band forming unit configured to form two elastic bands having an indefinite extension in the longitudinal direction, at least one of which comprises a succession of elastic sections separated from each other by transverse cuts, and joined together by refastenable closure formations, an elastic band application unit configured to overlap said elastic bands to respective side portions of the continuous absorbent composite web, and to fix the elastic bands to the continuous absorbent composite web along junction lines that are inclined with respect to the longitudinal axis, a cutting device configured to cut the continuous absorbent composite web and the elastic bands along cutting lines so as to give rise to a continuous succession of absorbent sanitary articles each having an absorbent body elongated in the longitudinal direction and having two front oblique sides and two rear oblique sides, and two elastic waistbands elongated in said longitudinal direction and fixed to the absorbent body along said front oblique sides and along said rear oblique sides, wherein each elastic band has a front section and a rear section separated from each other by a transverse cut and joined together by refastenable closure formations.

7. The apparatus according to claim 6, wherein said elastic band forming unit comprises a first cutting device configured to transversely cut longitudinal elastic threads of said continuous elastic bands.

\* \* \* \* \*

UNITED STATES PATENT AND TRADEMARK OFFICE
CERTIFICATE OF CORRECTION

PATENT NO. : 11,723,815 B2
APPLICATION NO. : 17/104012
DATED : August 15, 2023
INVENTOR(S) : Gabriele Sablone It is certified that error appears in the above-identified patent and that said Letters Patent is hereby corrected as shown below:

On the Title Page

(71) Applicant address information should be listed as:
- Fameccanica.Data S.p.A., San Giovanni Teatino (Chieti), ITALY -

(72) Inventor address information should be listed as:
- Gabriele Sablone, San Giovanni Teatino (Chieti), ITALY -

(73) Assignee address information should be listed as:
- Fameccanica.Data S.p.A., San Giovanni Teatino (Chieti), ITALY -

Signed and Sealed this
Twenty-sixth Day of March, 2024

Katherine Kelly Vidal
*Director of the United States Patent and Trademark Office*